United States Patent
Morris et al.

(10) Patent No.: US 8,957,111 B2
(45) Date of Patent: *Feb. 17, 2015

(54) STRONTIUM (M) ASCORBATE, COMPOSITIONS CONTAINING SAME, METHOD FOR MAKING SAME AND METHOD OF USING SAME

(71) Applicant: Nutraceutical Corporation, Park City, UT (US)

(72) Inventors: Shayne Morris, South Ogden, UT (US); Richard Bush, Ogden, UT (US)

(73) Assignee: Nutraceutical Corporation, Park City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/764,709

(22) Filed: Feb. 11, 2013

(65) Prior Publication Data

US 2013/0237509 A1 Sep. 12, 2013

Related U.S. Application Data

(63) Continuation of application No. 12/155,325, filed on Jun. 2, 2008, now Pat. No. 8,372,992.

(60) Provisional application No. 60/924,860, filed on Jun. 1, 2007.

(51) Int. Cl.
  *A61K 31/341* (2006.01)
  *C07D 307/34* (2006.01)
  *C07D 307/62* (2006.01)

(52) U.S. Cl.
  CPC .................................. *C07D 307/62* (2013.01)
  USPC ........... 514/474; 549/210; 549/295; 549/315; 514/449; 514/461

(58) Field of Classification Search
  CPC ........................... A61K 31/341; C07D 307/34
  USPC ........... 549/210, 295, 315; 514/449, 461, 474
  See application file for complete search history.

(56) References Cited

U.S. PATENT DOCUMENTS

| | | | |
|---|---|---|---|
| 8,372,992 B2 * | 2/2013 | Bush et al. | 549/315 |
| 8,378,126 B2 * | 2/2013 | Morris et al. | 549/315 |
| 8,609,169 B2 * | 12/2013 | Chen et al. | 426/321 |

* cited by examiner

*Primary Examiner* — Golam M M Shameem
(74) *Attorney, Agent, or Firm* — Terrence J. Edwards; TechLaw Ventures, PLLC

(57) ABSTRACT

A compound of formula (ascorbate)$_2$Sr:(M$^{+a}$)$_x$(ascorbate)$_y$, or ascorbate)$_2$Sr:Ca(ascorbate)$_2$, a composition containing the same, a method of making the same and a method of administering the same as a supplement.

17 Claims, 2 Drawing Sheets

STRONTIUM (M) ASCORBATE, COMPOSITIONS CONTAINING SAME, METHOD FOR MAKING SAME AND METHOD OF USING SAME

CROSS-REFERENCE TO RELATED APPLICATION

This application is a non-provisional U.S. utility patent application claiming priority to provisional U.S. application No. 60/924,860 filed before the U.S. Patent and Trademark Office on Jun. 1, 2007. The entire contents of provisional U.S. application No. 60/924,860 are incorporated herein by reference including its specification, claims, abstract and drawing figures for all purposes.

Because the anniversary date of the filing of the provisional U.S. application fell on Sunday, Jun. 1, 2008, the filing of this counterpart non-provisional U.S. utility patent application is timely as being filed on Monday, Jun. 2, 2008.

BACKGROUND

1. Field

The presently claimed invention is directed to strontium (M) ascorbate compound(s), compositions containing the same, method(s) for making the same and method of using the same. More particularly, for example, strontium (M) ascorbate may be used as a dietary supplement. As a further example, the dietary supplement may be used to administer an increased level of ascorbate to a subject in need thereof and/or to a subject to provide ascorbate as a dietary supplement.

2. Description of the Related Art

The nutritional value of ascorbic acid (vitamin C) is well known and its benefits have long been established. Most animals have a liver enzyme, which enables them to manufacture vitamin C in situ, by conversion of sugar into ascorbic acid. However, humans do not have this enzyme. Furthermore, humans are incapable of storing vitamin C, partly because it is metabolized and secreted and partly because it is a water-soluble vitamin.

Because humans lack the biochemical mechanism to produce vitamin C, it has to be obtained through food and/or nutritional dietary supplementation. Vitamin C is found in many fruits and vegetables, but it can also be supplemented into a number of dietary products including food, beverages, and dietary supplements.

Vitamin C has been implicated in more than 300 biological processes. The more important roles include the co-reaction with enzymes in the formation of collagen, the anti-scorbutric effect, the antioxidant and free radical scavenging reactions, energy metabolism accentuation in polynuclear leukosites and facilitation of iron absorption, among others.

The importance of vitamin C has been elucidated through understanding health complications which arise when vitamin C levels are deficient. Vitamin C deficiency can lead to a variety of conditions such as abnormal bleeding of the skin, mucous membranes, internal organs and muscles (due to impaired capillary integrity), hemorrhages, edema, joint pain, anorexia, and impaired wound healing (Mahan, L. K. and Arlin, M. T. Therapy 8$^{th}$ edition Philadelphia W.B. Saunders; Anderson, W. A. D. 1971 and Pathology 6$^{th}$ edition St. Louis, The C. V. Mosby Company).

Conversely, it has been shown that Vitamin C is well tolerated by humans and can safely be taken in mega-doses as noted by the nobel laureate Linus Pauling (J. S. Roe, Standard Method of Clinical Chemistry, edited by Seligson D. New York, Academic Press, 1961, Vo. 3, p. 35).

Clinical studies suggest that ascorbic acid participates in hydroxylation reactions associated with cholesterol metabolism (Ginter, E. "Cholesterol: Viamin C controls its Transformation to Bile Acids" Science 1973, 179:702-704). Humans can convert cholesterol into bile acids through a series of biochemical reactions. This allows the body to rid itself of excess cholesterol. Another more notable benefit of vitamin C is the formation of protocollagen through hydroxylation of proline and lysine. The enzyme hydroxylase forms the bonds with proline and collagen uses ascorbic acid as the reductant.

Strontium is a group (IIA) element similar in many ways to calcium, the most obvious being they are both divalent cations. Because strontium is a divalent cation, like calcium, without being bound by theory, it is thought that strontium is incorporated into bone mineralization via a similar mechanism to that related to calcium. In fact, also without being bound by theory, humans physiologically incorporate strontium into bone matrices altering the bone apatite. A primary feature reported was that $Sr^{+2}$ was incorporated in bone matrices at a site normally occupied by calcium (Esteve, M. J., Farre, R., Frigola, A. Garcia-Cantabella, J. M. Determination of Ascorbic and Dehydroascorbic acids in Blood Plasma and Serum by Liquid Chromatography. Journal of Chromatography 688 (1997) 345-349). Epidemilogical studies suggest strontium plays a possible role in reducing dental caries (Curzon M E J, (An association between strontium in drinking water supplies and low caries prevalence in man, Arch Oral Bio 23:317-321 (1978)). Investigations following moderate oral dosing of $SrCl_2$ indicated that strontium does not lower the serum and soft tissue levels of calcium (Skoryna. S. The Handbook of Stable Strontium, Plenum Press, New York, pp 11-617 (1966)). Additionally, it has also been shown that strontium stimulated bone formation in organ and cell cultures of rat calvariae (Vandecasteel, C., Vanhoe, H., and Dams, R., Determination of Strontium in Human Serum by Inductively Coupled Plasma Mass Spectrometry and Neutron Activation Analysis: A Comparison, Atlanta, 1990, (37): 8, 819-823). There have been a number of positive clinical results suggesting the relationship between strontium supplementation and bone health, particularly in relation to bone turnover at menopause (Vandecasteel, C., Vanhoe, H., and Dams, R. Determination of Strontium in Human Serum by Inductively Coupled Plasma Mass Spectrometry and Neutron Activation Analysis: A Comparison, Atlanta. 1990. (37): 8, 819-823). See also US Pub. No. 2006/0122274 A1 to Hansen et al. published Jun. 8, 2006, entitled "WATER-SOLUBLE STRONTIUM SALTS FOR USE IN TREATMENT OF CARTILAGE AND/OR BONE CONDITIONS" as well as the following references:

Meunier. P. J., et. al. Strontium Renelate: Dose-Dependant Effects in Established Postmenopausal Vertebral Osteoporosis-A 2-Year Randomized Placebo Controlled Trial. The Journal of Clinical Endocrinology & Metabolism 2002, 87(5):2060-2066; and Anderson, R I, 1981 Ascorbic acid and Immune Functions: Mechanism of Immunostimulation in Vitamin C (Ascorbic acid) by Counsell. J. M. and Hornig, S. H. 249-272. New Jersey, Applied Science Publishers.

SUMMARY

One or more aspects and/or advantages will be set forth, in part, in the description which follows and, in part, will be apparent from the description, or may be learned by practice of the invention.

According to an embodiment, the compound of formula (1) is:

(ascorbate)$_2$Sr:(M$^{+a}$)$_x$(ascorbate)$_y$ wherein ascorbate refers to the ascorbate anion:

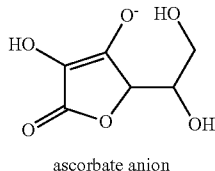
ascorbate anion where y is a positive integer, where x is a positive integer, where a is a positive integer reflecting the valence of M; where (y)=((x) multiplied by (+a)) such that a total positive charge ((x) multiplied by (+a)) equals a total negative charge (y) provided that the ascorbate anion has a negative valence of (−1); and where M is an alkali metal. an alkali earth metal or Mn, Cu, Zn, Fe and a combination thereof. M may also be Na, K. Mg, Ca and combinations thereof.

According to an embodiment, a method for making the compounds of formulas (1), (2) and/or (2-a) described herein may include the following steps conducted in any order sufficient to yield the desired product:

(a) dissolving at least a stoichiometric amount of ascorbic acid in water at a first solution temperature sufficient to dissolve the ascorbic acid in a solution;

(b) adding at least a stoichiometric amount of strontium carbonate (SrCO$_3$) to the solution of ascorbic acid;

(c) adding at least a stoichiometric amount of M carbonate (M$^{+a}$)$_{X1}$(CO$_3$)$_{y1}$ to the solution having a second solution temperature, where (+a)×(x1)=(−2)×(y1), where x1 is an integer and y1 is an integer;

(d) adjusting the second solution temperature within a range from about 40° C. to about 80° C. for a time sufficient to form the compound of formula (1); and (e) optionally, drying the slurry at a drying temperature and for a drying time sufficient to yield at least the compound of formula (1) in solid or semi-solid form.

According to yet another embodiment, optionally, calcium threonate may be added to the solution before step (d), before step (c) or before step (b). Alternatively, the calcium threonate may be added at any point of the above-noted method so long as such addition does not interfere (or substantially interfere) with the formation of the desired product. The desired product may be the compound of formulas (1), (2) and/or (2-a) in a desired purity.

According to a further embodiment, the compound of formulas (1), (2) and/or (2-a) may be provided in an oral dosage form together with a pharmaceutically acceptable excipient.

According to a further embodiment, the compound of formulas (1), (2) and/or (3) may be administered to a subject in need thereof or to a subject desiring to supplement the diet with the same. The subject may be a human or an animal.

BRIEF DESCRIPTION OF THE DRAWINGS

One or more aspects and/or advantages will become apparent and more readily appreciated from the following description of one or more embodiments, when taken in conjunction with the accompanying drawings of which.

DETAILED DESCRIPTION OF THE EMBODIMENT(S)

Figure 1:
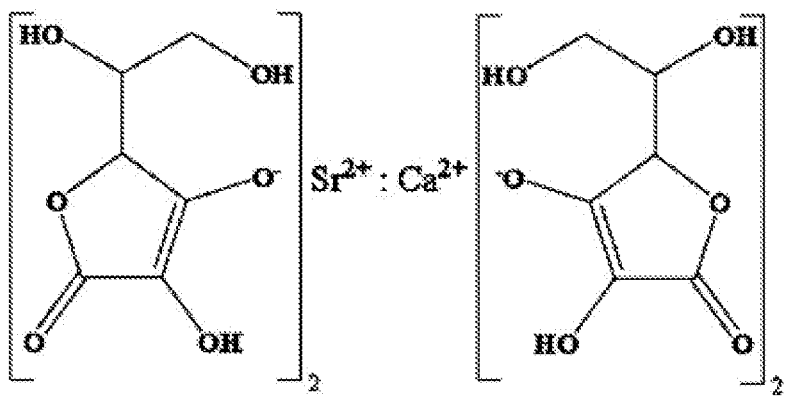
FIG. 1 depicts a theoretical structure of strontium calcium ascorbate.

Reference will now be made in detail to one or more embodiments.

Generically, the compound(s) of interest in connection with this disclosure are encompassed by the following general formula (1):

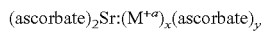
(ascorbate)$_2$Sr:(M$^{+a}$)$_x$(ascorbate)$_y$ wherein ascorbate refers to the ascorbate anion (or equivalents thereof including all its tautometric forms):

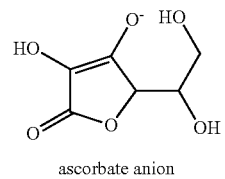
ascorbate anion which in its ascorbic acid form is depicted as:

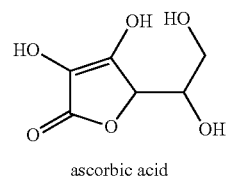 [SMILES: O=C1OC(C(O)CO)C(O)=C1O]
ascorbic acid wherein y=(x) multiplied by (+a) so that the total charge ((x) multiplied by (+a)) equals (y) being that the ascorbate anion has a single negative valence of (−1);

wherein y is a positive integer (e.g., 1, 2, 3, 4, 5, 6 or more), x is a positive integer (1, 2, 3, 4, 5, 6 or more) and a is a positive integer (e.g., 1, 2, 3, 4, 5, 6 or more) reflecting the valence of M; and wherein M is an alkali metal (e.g., Na or K or a combination thereof) or an alkali earth metal (e.g., Mg or Ca or a combination thereof) or Mn, Cu, Zn, Fe and/or a combination thereof.

According to an embodiment, a compound of interest is that of formula (2):

(ascorbate)$_2$Sr:Ca(ascorbate)$_2$ having (without being bound by theory) the theoretical structure depicted as formula (2-a):

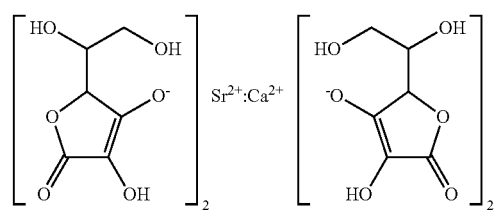

The process for making the compound of formula (2) includes the following steps:
- (a) dissolving at least a stoichiometric amount of ascorbic acid in water (e.g. distilled water) at a temperature sufficient to dissolve the ascorbic acid (e.g., dissolve in distilled water at 90° C. in an appropriate reaction vessel such as a Mueller reaction vessel);
- (b) adding at least a stoichiometric amount of strontium carbonate ($SrCO_3$) to the above-noted solution of ascorbic acid (e.g., preferably slowly adding the strontium carbonate in powder form);
- (c) adding at least a stoichiometric amount of calcium carbonate ($CaCO_3$) to the above noted reaction vessel (e.g., preferably slowly adding the calcium carbonate in powder form)—noting that the stochiometric amount in moles of Sr and moles of Ca will depend upon the ratio of moles of Sr to the moles of Ca used, so that the total stochiometric amount in moles of ascorbate will be at least twice the number of (moles of Sr+moles of Ca)—to form a slurry;
- (d) adjusting the slurry temperature in a range from about 40° C. to about 80° C. (e.g., 40-80° C., from about 45° C. to about 75° C., 45-75° C., from about 50° C. to about 70° C., 50-70° C., from about 55° C. to about 65° C., 55-65° C., from about 58° C. to about 62° C., 58-62° C., from about 59° C. to about 60° C., or 59-60° C.) for a time (e.g., 10 minutes, 20 minutes, 30 minutes, 40 minutes, 50 minutes, 1 hour, 2 hours, or increments thereof as needed depending on the size of the batch of slurry) sufficient to form the compound of formula (2); and
- (e) drying the slurry at a drying temperature and for a drying time sufficient to yield at least the compound of formula (2) in solid form (e.g, powder, cake, and/or other suitable form etc.).

According to another embodiment, the compound of formula (1) may be formed according to the above-noted process except that instead of ($CaCO_3$) either $(M^{+a'})_{x'}(CO_3)_{y'}$, where (x') multiplied by (+a')=(y') or $(M^{+a'})_{x'}(anion^{-b})_{y'}$, where (x') multiplied by (+a')=(-b) multiplied by (y') may be used. Note that (+a') is a positive integer (e.g. 1, 2, 3, 4, 5, 6 or more) and reflects the valence of the metal (M), that (−b) is a negative integer (e.g. −1, −2, −3, −4, −5, −6 or less) and reflects the valence of the anion (e.g., chloride, carbonate. etc.). According to yet another embodiment, optionally, calcium threonate may be added to the solution before step (d), before step (c) or before step (b). Alternatively, the calcium threonate may be added at any point of the above-noted method so long as such addition does not interfere (or substantially interfere) with the formation of the desired product. The desired product may be the compound of formulas (1), (2) and/or (2-a) in a desired purity (e.g., 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or better, respectively).

According to a further embodiment, the compound of formulas (1), (2) and/or (2-a) may be provided in an oral dosage form together with a pharmaceutically acceptable excipient. See Remington's Pharmaceutical Sciences, 16$^{th}$ Edition, A. Osol, Ed., Mack Publishing Co., Easton, Pa. (1980) and all later editions of the same. The composition may be an oral dosage form selected from the group consisting of a tablet, a capsule, a softgel capsule, a liquid, a syrup, a suspension, a sublingual tablet, a powder, and a lozenge. The oral dosage form may be an immediate release dosage form or an extended release dosage form.

Moreover, in step (a) any solvent other than water may be used that is suitable for forming the desired product of formulas (1), (2) and/or (2-a). Thus, for example, ethanol may be used instead of water with the proper temperature and time adjustments to those recited in steps (c), (d) and/or (e) as would be well within the knowledge of one of ordinary skill in the art in conjunction with this disclosure. Also, the above noted temperatures refer to temperatures at 1 atm pressure. However, if lower or higher pressures are used, then the temperatures and times in steps (c), (d) and/or (e) may be appropriately raised or lowered as would be well within the knowledge of one of ordinary skill in the art in conjunction with this disclosure.

According to another embodiment, appropriate stoichiometric amounts of the moles of Sr salts and/or Ca salts may be used to yield the compound of formula (2) wherein the ratio of the moles of Sr to the moles of Ca may be anyone of the following, including but not limited to, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 2.25, 2.5, 2.75, 3, or 4. Also the amount of water or other solvent to form the slurry may be adjusted as needed to achieve the appropriate ratio ranging from 0.1 to 4 and the heating, temperature and pressure conditions may be adjusted accordingly to yield the desired product. Further, the stoichiometric amount of ascorbate, ascorbate salt, and/or ascorbic acid used may be adjusted to provide that amount at least needed to react with the Sr salts and/or Ca salts used according to the above-noted process and description provided herein.

According to another embodiment, appropriate stoichiometric amounts of the moles of Sr salts and/or M salts may be used to yield the compound of formula (1) wherein the ratio of the moles of Sr to the moles of M may be anyone of the following, including but not limited to, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 2.25, 2.5, 2.75, 3, or 4. Also the amount of water or other solvent to form the slurry may be adjusted as needed to achieve the appropriate ratio ranging from 0.1 to 4 and the heating, temperature and pressure conditions may be adjusted accordingly to yield the desired product. Further, the stoichiometric amount of ascorbate, ascorbate salt, and/or ascorbic acid used may be adjusted to provide that amount at least needed to reach with the Sr salts and/or M salts used according to the above-noted process and description provided herein.

The water used may be distilled water, deionized water or any other form of water that does not interfere (or does not substantially interfere) with the synthetic steps necessary to form the desired product e.g., compounds of formulas (1), (2) and/or (2-a).

According to yet another embodiment, between steps (c) and (d), optionally, calcium threonate may be added to the slurry such that the amount of calcium threonate added is from about 1% to about 5% by weight of the final total weight of the desired product (including the weight of the calcium threonate) of formulas (1), (2) and/or (2-a) in dry form.

According to an embodiment, a suitable manufacturing method for the compounds include using a pure form of L-ascorbic acid, strontium carbonate and anyone of the other metal carbonates (or other suitable salts) of calcium, magnesium, manganese, zinc, copper, sodium, potassium, and iron. For example, the vitamin C (ascorbic acid) is dissolved in water and heated to between 60-100° C. To convert the vitamin C into the corresponding salt, the strontium and other mineral carbonates are added in at least the stoichometrically needed amounts to yield the compounds of formulas (1), (2) and/or (2-a).

Using the methodology described herein, the resulting compounds of formulas (2) and/or (2-a) match the standardized Fourier Transformed Infrared Spectroscopy (FTIR) scan with a high correlation. Also, the compounds of formulas (2) and/or (2-a) so made have an ascorbic acid value that ranges from 705-770 mg/g assayed by High Performance Liquid Chromatography (HPLC), a strontium value of 100-130 mg/g assayed by Inductively Coupled Plasma Optical Emissions Spectroscopy (ICP-OES), and the remaining mineral component has a value of 30-50 mg/g assayed by ICP-OES. The ranges of all three components may change because of the varying molecular weights and formulated ratios. However, the overall stoichiometry are two moles of vitamin C to one mole of a divalent mineral e.g. strontium, M, Ca, etc.

The analytical procedures utilized are described in: Clinical Chemistry, Principles and Techniques, edited by Richard J. Henry. Donald D. Cannon and James W. Windelman, Harper and Row, 1974 p. 1393-1398.

Below are provided non-limiting examples of certain aspects of the invention.

Example 1

Strontium Ascorbate (M) Salt Manufacturing Process

The following reaction is carried out to form a strontium (M) ascorbate salt using ascorbate, strontium and calcium where the Sr:Ca mole ratio is 0.6 moles Sr:0.4 moles Ca. Ascorbic acid is dissolved in distilled $H_2O$ at 90° C. in an appropriate reaction vessel (Meuller). The water mass is 10-25% of the mass of ascorbic acid. As soon as the ascorbic acid is dissolved, slowly add strontium carbonate followed by calcium carbonate. Keep temperature constant. As the reaction proceeds, add 0.5-5% water by mass. Reduce temperature to 60° C. 10 minutes after the last of the mineral salt is added. The resulting slurry is transferred to trays and placed in the oven at 60° C. until dry. Optionally, the strontium ascorbate (M) salt may need to be turned over once as part of the drying process. The dry strontium ascorbate (M) salt mass can be milled to varying particle sizes including a fine powder or a granular powder for use in various oral dosage forms.

Example 2

Testing and Qualification of the Final Powder Includes Sensory (Color, Taste, Appearance), pH, FTIR, HPLC, ICP-OES and ICP-MS Analytical Testing:

An FTIR method was developed to follow the reaction between the ascorbic acid and the mineral carbonates. Samples at various time points following addition of the mineral carbonates to the dissolved ascorbic acid were collected at time zero, 1 minute, 5 minutes, 10 minutes, 15 minutes, 30 minutes and 60 minutes and scanned using FTIR. The change in spectra was monitored and used to determine optimal reaction periods. Specifically, changes in the carbonyl, and carboxyl group peaks were followed.

The HPLC method was developed from Esteve, M. J., et. al., cited herein with modifications. Prior to the actual bioavailability analysis blood samples were drawn and spiked with known concentrations of ascorbic acid. Separation, accuracy, precision and limit of detection were estimated based on multiple injections of standards and spiked samples.

The ICP method was developed from Vandecasteel, C., et. al., cited herein with modifications. Prior to the actual bioavailability, analysis blood samples were drawn and spiked with known concentrations of strontium. Accuracy, precision and limit of detection were estimated based on multiple injections of standards and spiked samples.

Example 3

Bioavailability Study

Blood samples are drawn into vacu-tubes containing heparin. These tubes are then centrifuged at 6000 rpm for 15 minutes. The serum was pulled from the top and aliquots are placed in HPLC vials or ICP-MS vials. The sample preparation and analysis takes place immediately following the blood drawn.

HPLC Sample Prep:

Reducing vial contents are 1000 of 0.01M DDT, 300 µl serum, 200 µl distilled $H_2O$ and 600 µl 10% (by volume) metaphosphoric acid. Non-reducing vial contents are 300 µl serum, 300 µl distilled $H_2O$ and 600 µl 10% (by volume) metaphosphoric acid. Ascorbic acid purchased from Sigma Aldrich was weighed into 100 ml distilled $H_2O$/10% by volume metaphosporic acid sufficient to provide serial dilutions ranging from 100 µg/ml to 4 µg/ml.

ICP Sample Prep

Approximately 100 mg of serum was weighed into 100 ml volumetric flask. The samples were diluted with 80 ml distilled $H_2O$, spiked with 10 ppb yttrium (Y) as an internal standard and diluted to volume with distilled water. The strontium content was determined at mass 88 and quantified against a 4 point standard curve, ranging from 0 to 10 ppb.

Study Protocol

Participants:

Eight health adults, 7 men and 1 woman, were recruited for the study. There ages ranged from 22 to 37. None of the participants were smokers currently; however, one of the men had been a smoker. They all consumed a healthy diet, and most of them regularly took vitamin and mineral supplements.

All participants were asked to refrain from taking nutritional supplements and eating foods high in ascorbic acid two days prior to each dosing. On the day of the dosing and plasma sampling, the participants did not consume any food until the last sample was taken.

Inclusion Criteria:

Subject and/or legal guardian of the subject willing to sign an Informed Consent Form, Assent Form if indicated, and a HIPAA Authorization Form.

Male and female subjects between the ages of 18 and 45 years and in generally good health.

Subjects who have not used dietary supplements or medications for 48 hours prior to start of study.

Subjects who agree not to use supplements or medicines that would interfere with vitamin C during the study.

Subjects who exhibit dependability and intelligence in following directions.

Exclusion Criteria:

Subjects who are sensitive to any of the ingredients in the test articles.

Subjects taking routine high dosage anti-inflammatory medications (aspirin, ibuprofen).

Subjects who cannot comply with the dietary requirements.

Any condition for which the Investigator determines that the subject could be placed under undue risk.

Samples:

Ascorbic acid samples were prepared in the following formulations:

1. 500 mg Ascorbic acid in a pink colored gelatin capsule.

2. 500 mg Ascorbic acid from (Magnesium, Zinc, Calcium, ascorbates) in a pink colored gelatin capsule.
3. 500 mg placebo (cellulose) in a pink colored gelatin capsule.

Figure 2A:
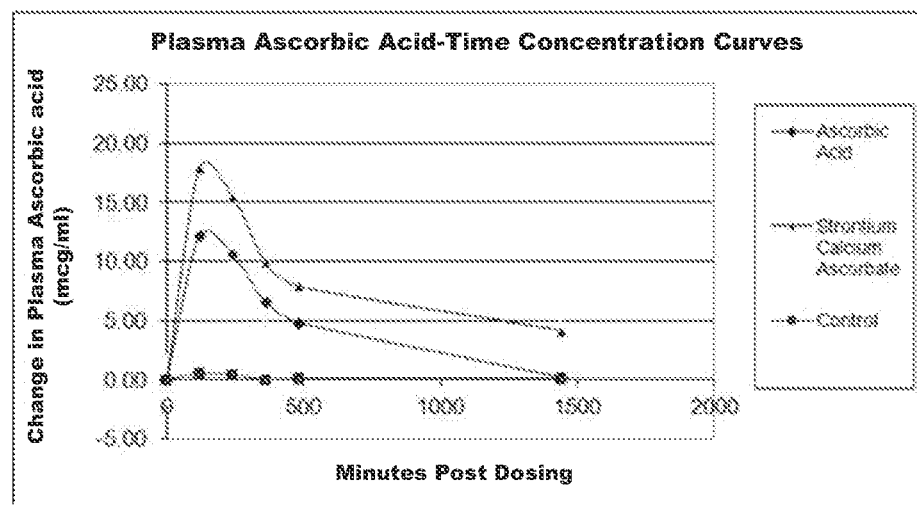
FIG. 2A is a plot of plasma ascorbic acid concentration versus time for control (placebo), ascorbic acid, and strontium calcium ascorbate.
Figure 2B:
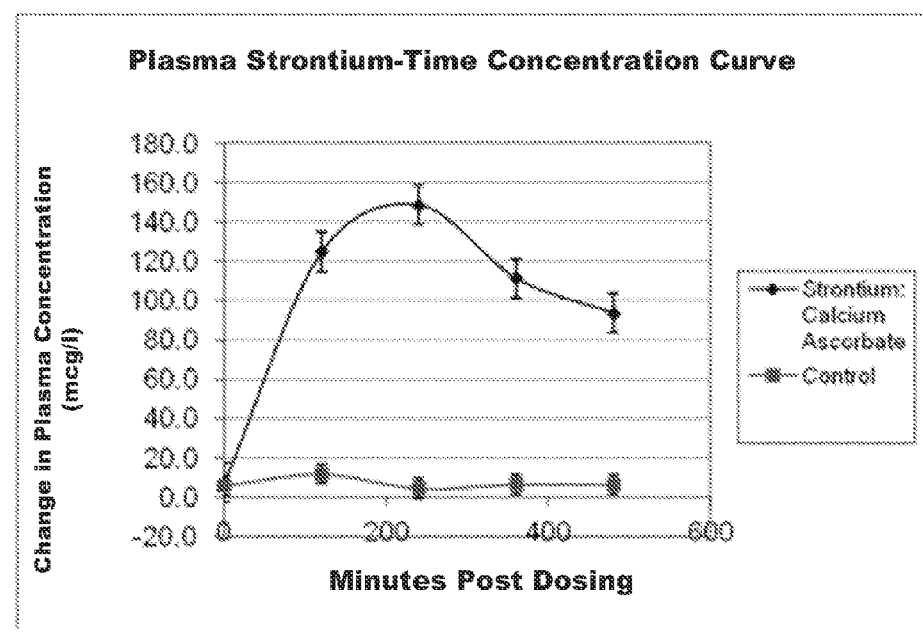
FIG. 2B is a plot of plasma strontium concentration versus time for control (placebo), and strontium calcium ascorbate.

Dosing/Sampling:

On the day of dosing each volunteer will consume 2 capsules of an ascorbic acid formulation or placebo. Blood will be drawn right before dosing and then 2, 4, 6, and 8 hours after dosing. The blood plasma will be separated by centrifugation and then split for mineral (when present) and Ascorbic acid testing. A 10% (by volume) metaphosphoric acid is added to the ascorbic acid test samples. Categories of drugs that can diminish the body's supply of vitamin C include: oral contraceptives (birth control pills), NSAIDs (non-steroidal anti-inflammatory drugs including aspirin), corticosteroids (like cortisone), sulfa drugs (often used as antibiotics or in cancer treatment), and barbituates. Results are illustrated in FIGS. 2A and 2B.

All patents, patent applications, all publications, and all references cited herein are incorporated herein by reference in their entirety for all purposes.

Although a few embodiments have been shown and described, it would be appreciated by those skilled in the art that changes may be made in these embodiments without departing from the principles and spirit of the invention, the scope of which is defined in the claims and their equivalents.

What is claimed is:

1. A compound of formula (1):

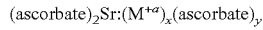

wherein ascorbate refers to the ascorbate anion:

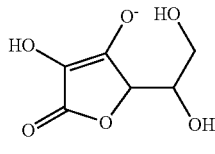

ascorbate anion wherein y is a positive integer, wherein x is a positive integer, wherein a is a positive integer reflecting the valence of M;
wherein (y)=((x) multiplied by (+a)) such that a total positive charge ((x) multiplied by (+a)) equals a total negative charge (y) provided that the ascorbate anion has a negative valence of (−1); and
wherein M is an alkali metal, an alkali earth metal or Mn, Cu, Zn, Fe and a combination thereof.

2. The compound of claim 1, wherein M is selected from the group consisting of Na, K, M, Ca, Mn, Cu, Zn, Fe and combinations thereof, wherein y is 1, 2, 3, 4, 5, or 6, wherein a is 1, 2, 3, 4, 5, or 6, and wherein x is 1, 2, 3, 4, 5, or 6.

3. The compound of claim 1 of formula (2):

wherein Sr refers to strontium and Ca refers to calcium.

4. The compound of claim 1, wherein the ratio of the moles of Sr to the moles of M is selected from the group consisting of, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 2.25, 2.5, 2.75, 3, and 4.

5. The compound of claim 3, wherein the ratio of the moles of Sr to the moles of Ca is selected from the group consisting of, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 2.25, 2.5, 2.75, 3, and 4.

6. A composition comprising the compound of formula (1) of claim 1 and a pharmaceutically acceptable excipient.

7. The composition of claim 6 in an oral dosage form selected from the group consisting of a tablet, a capsule, a softgel capsule, a liquid, a syrup, a suspension, a sublingual tablet, a powder, and a lozenge.

8. The composition of claim 7 wherein the oral dosage form is an immediate release dosage form or an extended release dosage form.

9. A composition comprising the compound of formula (2) of claim 3 and a pharmaceutically acceptable excipient.

10. The composition of claim 9 in an oral dosage form selected from the group consisting of a tablet, a capsule, a softgel capsule, a liquid, a syrup, a suspension, a sublingual tablet, a powder, and a lozenge.

11. The composition of claim 10 wherein the oral dosage form is an immediate release dosage form or an extended release dosage form.

12. A method of providing ascorbic acid comprising administering the composition of claim 6 to a subject.

13. The method of claim 12 wherein the subject is in need of the composition of claim 6 and the subject is a human.

14. A method of providing ascorbic acid comprising administering the composition of claim 9 to a subject.

15. The method of claim 14 wherein the subject is in need of the composition of claim 6 and the subject is a human.

16. The compound of claim 1 in a solid form selected from the group consisting of a powder form, a granular form or a cake form.

17. The compound of claim 1, wherein a ratio of the moles of strontium to the moles of M is such that strontium is present in an amount that is more than or equal to the amount of M.

* * * * *